United States Patent
Makker et al.

(10) Patent No.: US 7,247,689 B2
(45) Date of Patent: Jul. 24, 2007

(54) BIOCOMPATIBLE POLYMERIC COMPOSITIONS FOR USE IN MAKING ANTERIOR CHAMBER INTRAOCULAR LENSES

(75) Inventors: Harish C. Makker, Mission Viejo, CA (US); Michael D. Lowery, Vista, CA (US); Can B. Hu, Irvine, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 11/219,021

(22) Filed: Sep. 1, 2005

(65) Prior Publication Data

US 2006/0004163 A1    Jan. 5, 2006

Related U.S. Application Data

(63) Continuation-in-part of application No. 10/856,297, filed on May 28, 2004, now abandoned.

(51) Int. Cl.
| | |
|---|---|
| *C08F 120/22* | (2006.01) |
| *C08F 20/22* | (2006.01) |
| *C08F 220/22* | (2006.01) |
| *C08F 18/20* | (2006.01) |

(52) U.S. Cl. ........................ 526/245; 526/242; 623/4.1; 623/6.11; 623/6.37

(58) Field of Classification Search ................ 526/245, 526/242; 623/4.1, 6.11, 6.37
See application file for complete search history.

(56) References Cited

U.S. PATENT DOCUMENTS

| | | | | |
|---|---|---|---|---|
| 4,834,750 | A  * | 5/1989 | Gupta ........................ 623/6.58 |
| 6,555,030 | B1 * | 4/2003 | Weinschenk, III ........... 264/1.7 |
| 6,638,305 | B2 * | 10/2003 | Laguette .................... 623/6.37 |
| 6,645,246 | B1 * | 11/2003 | Weinschenk et al. ...... 623/6.37 |
| 2004/0192872 | A1 | 9/2004 | Iwata et al. |

FOREIGN PATENT DOCUMENTS

EP    1 243 960 A1    9/2002

\* cited by examiner

*Primary Examiner*—Ling-Sui Choi

(57) ABSTRACT

Biocompatible polymers useful for making anterior chamber intraocular lenses (AC-IOL) are provided. The biocompatible polymers are generally composed of one or more acrylate monomers, crosslinked with at least one diacrylate ester and may include one or more additional components such as ultraviolet light and/or blue-violet light absorbing dyes. The AC-IOLs made using the biocompatible polymers disclosed herein are suitable for placement in phakic or aphakic eyes and are intended for refractive correction including myopia, hyperopia, presbyopia and astigmatisms.

20 Claims, No Drawings

BIOCOMPATIBLE POLYMERIC COMPOSITIONS FOR USE IN MAKING ANTERIOR CHAMBER INTRAOCULAR LENSES

CROSS REFERENCE TO RELATED APPLICATIONS

This application is a continuation-in-part of U.S. patent application Ser. No. 10/856,297 filed May 28, 2004 now abandoned.

FIELD OF THE INVENTION

The present invention generally relates to biocompatible polymeric compositions. Specifically, the biocompatible polymeric compositions of the present invention are useful for fabricating intraocular lenses (IOL). More specifically the biocompatible polymeric compositions are intended for making anterior chamber intraocular lenses (AC-IOL).

BACKGROUND OF THE INVENTION

Intraocular lenses (IOLs) were first used as a replacement for damaged natural crystalline lenses in 1949. These early IOLs were implanted into the posterior chamber after the natural crystalline was surgically removed. The first physician to use posterior chamber IOLs as replacements for the natural crystalline lens was English RAF ophthalmologist Dr. Howard Ridley. Dr Ridley first observed acrylate polymer biocompatibility in the eyes of pilots who had sustained ocular injuries from polymethylmethacrylate (PMMA) shards when their aircraft canopies were shattered. However, it took nearly thirty years for ophthalmologists to embrace IOL implantation as a routine method for restoring vision in patients suffering from diseased or damaged natural crystalline lenses.

Early IOLs were made from PMMA because of its proven biocompatibility. Polymethylmethacrylate is a ridged polymer and requires a 5 mm to 7 mm incision. Incision size is directly related to patient trauma, discomfort and healing times. Moreover, incisions sizes in the 5 mm to 7 mm range generally require sutures further increasing procedural complexity and patent discomfort. Lens size dictates incision size and lens size is in turn determined by the size of the capsular sac and natural crystalline lens. Thus lenses made from a rigid polymer such as PMMA require an incision size at least as large as the minimum IOL dimension which is generally 5.5 mm on average.

In an effort to decrease incision size and corresponding patient discomfort, recovery time and procedural complexity, a number of IOL designs suitable for insertion through small incisions have been developed; most notably foldable IOLs. Foldable IOLs are made from non-rigid, or pliable polymers including hydrophobic acrylics, hydrophilic hydrogels, silicone elastomers and porcine collagen. Intraocular lenses made form these materials can be folded or rolled into implantable configurations having minimum dimensions suited for 3 mm incisions, or less.

Traditionally, IOLs have been exclusively used to restore vision to patients having damaged natural crystalline lenses or cataracts. These generally involved implanting a polymeric IOL into the capsular sac in the eye's posterior chamber after the damaged natural crystalline lens was surgically removed. Recently, refractive correction using IOLs in the phakic eye has grown in popularity as an option to refractive laser surgery. However, there are difficulties associated with implanting an IOL in the phakic eye that are not encountered when implanting a lens in the aphakic eye. The phakic eye is a substantially more reactive environment than the aphakic eye. Inflammatory reactions tend to be greater in the phakic eye resulting in a concomitant increase in damage to the eye caused by implanting intraocular lenses. Moreover, the presence of the natural lens in the phakic eye significantly reduces the space available for posterior chamber implantation. Thus, an IOL implanted into the posterior chamber of the phakic eye will directly contact the posterior surface of the natural crystalline lens. Under some circumstances this can result in permanent injury to the natural crystalline lens. Consequently, efforts to implant a refractive correcting IOLs into the eye's anterior chamber have been developed.

The anterior chamber of an eye is that area in front of the iris and behind the cornea. The iris separates the anterior chamber and the posterior chamber and thus IOLs implanted into the anterior chamber of the phakic eye rest against the iris not the natural crystalline lens. However, the phakic eye has a narrow anterior chamber thus lenses implanted in the anterior chamber must be thinner than those used in the posterior chamber. Moreover, it is desirable to minimize the incision size used to implant the anterior chamber IOL for the reasons discussed above. Consequently, the anterior chamber IOL must be at least as pliable as a posterior chamber IOL but must be thinner. Unfortunately, this combination of attributes has proven to be exceeding difficult to obtain. Lenses made thin and pliable enough to fit comfortably into the eye's anterior chamber lack the mechanical strength (resiliency) necessary to withstand casual contact or impact injuries such as those experienced in every day life. Anterior chamber IOLs made strong enough to resist incidental impact damage are generally thicker and thus must be inserted through larger incisions and are generally limited to minus refractive corrections, or extremely limited in the degree of positive correction possible.

Therefore, there is a need for biocompatible polymeric compositions that can be used to make an anterior chamber IOL that are thin and pliable enough to fit easily through small incisions, have sufficient mechanical strength to resist impact-related damage and can be made in a wide range of diopters sufficient to provide refractive correction for myopia, hyperopia, presbyopia and astigmatisms.

SUMMARY OF THE INVENTION

The present invention is directed to intraocular lenses, specifically intraocular lenses (IOL) suitable for placement in the anterior chamber of the phakic or aphakic eye. The anterior chamber intraocular lenses (AC-IOL) of the present invention are intended for refractive correction and are suitable for correcting myopia, hyperopia, presbyopia and astigmatisms. In one embodiment of the AC-IOLs of the present invention the AC-IOLs are positioned within the anterior chamber of a phakic eye such that they do not contact the cornea's posterior surface or the natural crystalline lens' anterior surface and are angle supported (i.e. rest against) by, but not attached to, the iris. The AC-IOLs of the present invention must be sufficiently pliable for small incision implantation and also resilient enough to recover quickly when deformed in the eye as the result of incidental contact. This combination of attributes (pliability and resilience) is unique to the AC-IOL and differs from similar attributes found in small incision-compatible PC-IOLs thus placing unique demands on the compositions used to make the AC-IOLs of the present invention.

In one embodiment of the present invention a biocompatible polymer is provided comprising approximately 50 mass percent to 55 mass percent of a first alkyl acrylate, approximately 29 mass percent to 32 mass percent of a second alkyl acrylate, approximately 9 mass percent to 11 mass percent of a fluoroacrylate, approximately 4 mass percent to 5 mass percent of a diacrylate ester crosslinking agent wherein the biocompatible polymer is used to form an anterior chamber intraocular lens (AC-IOL). The first alkyl acrylate and said second alkyl acrylate are selected from the group consisting of methacrylate, ethyl methacrylate, n-butyl acrylate, ethyl acrylate and 2-ethyl hexyl acrylate, providing that said first acrylate ester is different than said second acrylate ester. Moreover, the diacrylate ester crosslinking agent used to make the AC-IOLs of the present invention are selected from the group consisting of ethylene glycol dimethacrylate, propylene glycol dimethacrylate, ethylene glycol diacrylate and combinations thereof.

The biocompatible polymer used in accordance with the teachings of the present invention incorporate a fluoroacrylate surface energy lowering monomer selected from the group consisting of perfluorooctal methacrylate, trifluoroethyl methacrylate and combinations thereof.

In at least one other embodiment of the present invention the AC-IOL will have at least one ultraviolet (UV) light absorbing compound and alternatively, or additionally, at least one blue-violet light absorbing compound.

In another embodiment of the present invention biocompatible polymer comprising approximately 50 mass percent to 55 mass percent of ethyl acrylate, approximately 29 mass percent to 32 mass percent of ethyl methacrylate, approximately 9 mass percent to 11 mass percent of trifluoroethyl methacrylate, approximately 4 mass percent to 5 mass percent of ethylene glycol dimethacrylate is used to form an anterior AC-IOL. This embodiment of the AC-IOL of the present invention may also comprise at least one ultraviolet (UV) light absorbing compound and/or a blue-violet light absorbing compound.

In yet another embodiment of the present invention an AC-IOL is provided consisting essentially of approximately 54 mass percent of ethyl acrylate, approximately 30 mass percent of ethyl methacrylate, approximately 10 mass percent of trifluoro methacrylate, and approximately 5 mass percent of glycol dimethacrylate wherein residual solvents and UV absorbing compounds make up the remaining mass percentage such that the total mass percent is 100.

In a preferred embodiment of the present invention a biocompatible polymer is provided comprising a first alkyl acrylate, a second alkyl acrylate, a fluoroacrylate, and a diacrylate ester crosslinking agent wherein said biocompatible polymer has a Tg of approximately 17° C., a tensile strength of approximately 1690 psi; an elongation at break of approximately 110% and is used to form an anterior chamber intraocular lens (AC-IOL). Moreover the AC-IOLs made in accordance with the teachings of the present invention have a refractive index ($n_D$) at 20° C.-25° C. of between approximately 1.40 and 1.50. In a preferred embodiment the AC-IOL has a refractive index ($n_D$) at 20° C.-25° C. of approximately 1.47.

DEFINITION OF TERMS

To aid in the understanding the following detailed description of the present invention, the terms and phases used herein shall have the following, non-limiting, definitions.

Aphakic: As used herein "aphakic" shall mean the condition where the natural crystalline lens has been removed form the eye, that is, an eye lacking its natural crystalline lens.

Mass percent: As used herein "mass percent" is defined as the mass of the solute in grams multiplied by 100 divided by the mass of the solution in grams i.e. mass %=mass of solute (in grams)(100)/mass of solution (in grams).

Mechanical strength: "Mechanical strength" is a subjective terms and as used herein refers to the sum of a polymer's physical properties that define a polymer's resiliency. Specifically, as used herein "mechanical strength" refers to the polymer's ability to resist tearing. Thus a polymer having suitable "mechanical strength" as defined herein will result in an IOL that deforms sufficiently to absorb impact stress yet does not tear. Moreover, the IOL will then quickly return to its pre-stressed shape after the source of the impact stress has been removed. As used herein an IOL made from a polymer having inadequate "mechanical strength" will result in a lens that is slow to rebound and return to its pre-stressed shape and is more prone to tear when stressed. In contrast, an IOL having to made from a polymer having too great of a "mechanical strength" will make the lens too rigid, or "stiff" and less responsive to stress and thus more prone to maintain its pre-stressed shape under strain and cause injury to the eye's delicate structures. Moreover, excessively rigid lens cannot be folded, rolled or otherwise sufficiently deformed to be inserted through small incisions.

Pliable: As used herein "pliable" means "flexible" and refers to a polymeric IOL that can be folded, rolled or otherwise deformed sufficiently to be inserted through a "small incision".

Phakic: As used herein "phakic" refers to an eye having the natural crystalline lens in place.

Residual solvents: As used herein "residual solvent(s)" refers to trace solvents that may be present in the polymer matrix after the AC-IOL formed from the solvents have been processed and are in final for suitable for deployment into the eye.

Resiliency: As used herein "resiliency" refers to a polymeric IOL having sufficient "mechanical strength" to return to its pre-stressed configuration following impact and the resulting deformation associated with the stress on impact, also referred to herein after as "rebound resiliency."

Softness: As used herein "softness" refers to a polymeric IOL that is resilient and pliable as opposed to a polymethylmethacrylate (PMMA) IOL that is rigid and hard.

Small incision: As used herein the term "small incision" refers to a surgical incision of less than approximately 5 mm made in the eye's cornea that permits the insertion of an IOL into the anterior chamber. Preferably the incision is less that 3 mm and even more preferably the incision is less than 2 mm.

DETAILED DESCRIPTION OF THE INVENTION

The present invention is directed to intraocular lenses, specifically intraocular lenses (IOL) suitable for placement in the anterior chamber of the phakic or aphakic eye. Traditional intraocular lenses are available in a wide range of biocompatible materials ranging from hard plastic compositions such as polymethylmethacrylate (PMMA) to soft highly flexible materials including silicones, certain acrylics and hydrogels. Recently the more pliable, or softer lenses have gained in popularity due to their ability to be compressed, folded, rolled and otherwise deformed. These more pliable IOLs can be inserted through much narrower incisions than hard PMMA lenses and thus reduce the healing time and discomfort associated with IOL implantation.

The majority of IOL procedures involve inserting an IOL into the posterior chamber (PC) or anterior chamber (AC) of an aphakic eye as a replacement for a damaged or diseased natural crystalline lens that has been surgically removed from the eye. While these lenses also possess refractive corrections, the primary purpose is to restore sight lost to the damaged or diseased natural lens. However, surgically implanted anterior chamber IOLs as a permanent form of refractive correction have recently gained popularity.

The anterior chamber intraocular lenses (AC-IOL) of the present invention are intended for refractive correction and are suitable for correcting myopia, hyperopia, presbyopia and astigmatisms. In one embodiment of the AC-IOLs of the present invention the AC-IOLs are positioned within the anterior chamber of a phakic eye such that they do not contact posterior of the cornea or natural crystalline lens and are angle supported (i.e. rest against) by, but not attached to, the iris. The AC-IOLs of the present invention must be sufficiently pliable for small incision implantation and also resilient enough to recover quickly when deformed in the eye as the result of incidental contact. This combination of attributes (pliability and resilience) is unique to the AC-IOL and differs from similar attributes found in small incision-compatible PC-IOLs thus placing unique demands on the compositions used to make the AC-IOLs of the present invention.

The eye's anterior chamber is a relatively small space compared with the posterior chamber and an AC-IOL must be positioned within this narrow space such that it does not contact the posterior surface of the cornea or the anterior surface of natural lens. Thus, the AC-IOLs of the present invention must be thinner than their PC-IOL counterparts. Moreover, in order to minimize patient discomfort and decrease recovery time, it is desirable to insert the AC-IOL through a small incision, preferably a 3 mm incision or less. This requires that the lens be pliable so that it easily deforms to reduce the pre-insertion size and yet resilient enough to gently unfold once implanted. However, because the AC-IOL of the present invention must also be thin enough to provide a suitable fit within the eye's anterior chamber, the material used to fabricate the AC-IOL must have sufficient mechanical strength to prevent the pliable AC-IOL from tearing during implantation or use.

Furthermore, because an AC-IOL is inserted in front of the iris and directly behind the cornea it is more vulnerable to compression injury caused by foreign objects contacting the eye than PC-IOLs. Consequently, an AC-IOL should be made from resilient materials that deform upon impact, thus absorbing the shock, yet quickly return to the AC-IOL's pre-compressed shape to restore normal vision. Lenses that are too rigid, such as PMMA AC-IOLs can damage the iris or scar the cornea because they do not compress on impact; however, lenses that are too soft (too pliable) are prone to permanently deform or tear due to their lack of resiliency (mechanical strength) and thus no longer provide the proper refractive correction. A factor that makes balancing pliability with mechanical strength is the need to minimize pupil ovalization. Pupil ovalization is a structural change characterized by a change in pupil shape from nearly perfectly round to oval and prevents the pupil from contracting and dilating normally. Pupil ovalization can result from oversized AC-IOL, haptic misalignment and iris fixation (where the AC-IOL is attached to the iris surgically) and is commonly associated with AC-IOLs that are stiff, rigid or hard such as PMMA AC-IOLs. The pupil ovalization is not associated with PC-IOLs. Therefore, an AC-IOL should have sufficient mechanical strength to absorb impact stress without tearing, and at the same time be sufficiently pliable to minimize pupil ovalization.

Therefore, the present invention provides polymeric compositions that balance the competing physical properties described above; namely, the polymer compositions of the present inventive are biocompatible, are pliable enough to be folded rolled or otherwise deformed sufficiently to be inserted through small incisions, possess sufficient mechanical strength that they can be shaped thinner than conventional PC-IOLs, have sufficient mechanical strength to provide rebound resiliency upon impact without tearing, yet not so stiff that the AC-IOL is prone to inducing pupil fixation.

The biocompatible polymers of the present invention are useful for the fabrication of AC-IOLs having the properties defined above. The present inventors have developed the disclosed biocompatible polymers specifically to achieve a pliable, resilient and durable AC-IOL that can be shaped to achieve refractive correction for a wide range of vision anomalies including myopia, hyperopia, presbyopia and astigmatisms. The narrowness of the anterior chamber in phakic eyes, especially hyperopic eyes, makes the surgical placement AC-IOL difficult. Therefore, it is desirable that the AC-IOL intended for use as both a positive and negative power ocular lens must be as thin as possible. Furthermore, it is desirable to have an AC-IOL that can be folded, rolled or otherwise deformed such that it can be inserted through a small incision in order to minimize patient trauma and post surgical recovery time. Thus, a thin, pliable polymeric AC-IOL is desirable. However, thin, pliable polymeric IOLs are generally extremely fragile and when placed in the eye's anterior chamber can be easily dislocated or damage by incidental contact such as a finger nails, make-up applicators or other small objects. In order to prevent lens dislocation or damage, it is possible to design polymers having greater mechanical strength. However, IOLs having too much mechanical strength may lack resiliency and thus not deform easily for insertion purposes, or may fail to absorb impact shock. Therefore, as discussed above, the ideal AC-IOL suitable for correction of hyperopia in addition to myopia needs to be thinner than conventional PC-IOLs or AC-IOLs intended solely to correct myopia and must also be pliable and resilient. In order to balance these seemingly competing objections and provide a versatile high performance AC-IOL for the phakic eye, the present inventions have developed a new polymer formulation.

In one embodiment of the present invention a biocompatible polymer is provided comprising approximately 50 mass percent to 55 mass percent of a first alkyl acrylate, approximately 29 mass percent to 32 mass percent of a second alkyl acrylate, approximately 9 mass percent to 11 mass percent of a fluoroacrylate, approximately 4 mass percent to 5 mass percent of a diacrylate ester crosslinking agent wherein the biocompatible polymer is used to form an anterior chamber intraocular lens (AC-IOL). The first alkyl acrylate and said second alkyl acrylate are selected from the group consisting of methacrylate, ethyl methacrylate, n-butyl acrylate, ethyl acrylate and 2-ethyl hexyl acrylate, providing that said first acrylate ester is different than said second acrylate ester. Moreover, the diacrylate ester crosslinking agents used to make the AC-IOLs of the present invention are selected from the group consisting of ethylene glycol dimethacrylate, propylene glycol dimethacrylate, ethylene glycol diacrylate and combinations thereof.

The biocompatible polymer used in accordance with the teachings of the present invention incorporates a fluoroacrylate surface energy lowering monomer selected from the group consisting of perfluorooctal methacrylate, trifluoroethyl methacrylate and combinations thereof.

In at least one other embodiment of the present invention the AC-IOL will have at least ultraviolet (UV) light absorbing compound and alternatively, or additionally at least one blue-violet light absorbing compound.

In another embodiment of the present invention biocompatible polymer comprising approximately 50 mass percent to 55 mass percent of ethyl acrylate, approximately 29 mass percent to 32 mass percent of ethyl methacrylate, approximately 9 mass percent to 11 mass percent of trifluoroethyl methacrylate, approximately 4 mass percent to 5 mass percent of ethylene glycol dimethacrylate; is used to form an anterior AC-IOL. This embodiment of the AC-IOL of the present invention may also comprise at least one ultraviolet (UV) light absorbing compound and/or a blue-violet light absorbing compound.

In yet another embodiment of the present invention an AC-IOL is provided consisting essentially of approximately 54 mass percent of ethyl acrylate, approximately 30 mass percent of ethyl methacrylate, approximately 10 mass percent of trifluoro ethylmethacrylate, and approximately 5 mass percent of glycol dimethacrylate wherein residual solvents and UV absorbing compounds make up the remaining mass percentage such the total mass percent is 100.

It is understood by those having ordinary skill in the art that other methods of synthetic polymer chemistry may be used to achieve the biocompatible polymeric compositions of the present invention and as such the following process in non-limiting. Moreover, persons having ordinary skill in the art will recognize that the materials used in the following process are readily available from many different commercial sources. However, the source of the materials used herein is not limiting.

Generally, the polymeric compositions of the present invention begin with preparing a reaction mixture having approximately 28 mass percent to 35 mass percent ethyl methacrylate and either n-butyl acrylate or preferably ethyl acrylate in a weight percent concentration of approximately 50 mass percent to 55 mass percent. In addition to the methacrylate and acrylate esters, the reaction mixture also includes approximately 10% by weight of a fluoroacrylate functioning as a surface energy lowering agent. Such fluoroacrylates may be perfluorooctal methacrylate or more preferably trifluoroethyl methacrylate. In the reaction mixture, the n-butyl acrylate or ethyl acrylate provides flexibility in the presence of methacrylate esters principally because of the low glass transition temperature thereof. However, the n-butyl acrylate or ethyl acrylate renders the mixture tacky or sticky. Such tackiness is minimized by the fluoracrylate particularly trifluoroethyl methacrylate. In addition to the foregoing, the reaction mixture may also include at least one an ultraviolet (UV) light absorber such as but not limited to the UV chromophores benzophenones and benzotriazoles-based compounds (for example Cyasorb® a registered trademark of Cytec Technology Corp. Wilmington, Delaware) and/or at least one blue-violet light absorbing dye as known to those skilled in the art. For example, and not intended as a limitation, suitable blue-light blocking dyes and monomers are found in U.S. Pat. No. 5,410,932, those portions of the specification describing blue-light blocking dyes and monomers are incorporated herein in their entirety. However, it is understood that many dye classes may be suitable for use as blue-light blocking agents and can be used in accordance with the teachings of the present invention.

In some embodiments a free radical initiator such as, but not limited to aliphatic peroxides may also be included. The UV-absorber, blue-violet light aborting dye and initiator are present at from approximately 0.05% to 5.0% by weight concentrations. The reaction mixture also includes initiator and at least one cross linking agent such as a diacrylate ester. The type and amount of cross linking agent is carefully selected to obtain the requisite degree of mechanical strength and pliability.

In one method for making the biocompatible polymers for the present invention a reaction mixture is prepared in a suitable reaction vessel such as a one liter three-neck round-bottom flask by carefully mixing approximately 28 to 35 weight percent ethyl methacrylate (EMA), approximately 50 to 55 weight percent ethylacetate (EA), approximately 10 weight percent 2,2,2-trifluoroethylmethacrylate (TFEMA) approximately 4 to 5 weight percent ethyleneglycol dimethacrylate (EGDMA), approximately 0.100 to 0.150 weight percent of a suitable thermal initiator, such as a peroxide including but not limited to di-tert-butyl peroxide (Trigonox® a registered trademark of Akzo Chemie Nederland B.V. Corporation Amersfoort, Netherlands) or 2,5-dimethyl-2,5-bis (2-ethylhexanoylperoxy) hexane and approximately 1.0 to 1.5 weight percent of Cyasorb® UV 416. The thermal imitator is generally added last after the reaction vessel is securely supported and provided with a mixing means such as a magnetic stir plate with stir bar or a low-shear impellor and overhead drive. Next nitrogen gas is gently (≈1 PSI) bubbled through the reaction mixture for approximately 15 minutes and the reaction mixture is degassed under vacuum (approximately 88±2 Torr) for five minutes. Because thermal initiated polymerization is exothermic it is important to maintain control over the reaction mixture. An immersion chiller water bath can be used to prevent the reaction mixture from overheating.

The AC-IOLs of the present invention are formed by transferring the biocompatible polymer reaction mixture into molds having the desired shape before the polymerization and cross linking reactions are complete. In one embodiment of the present invention molds are provided to receive the liquid reaction mixture. The molds are first brought to a suitable temperature that permits the polymer lens to cure in a controlled manner. In one embodiment of the present invention a water bath is used to maintain mold temperature at approximately 78° C.±2° C. One non-limiting means for transferring the reaction mixture to the molds is by increasing the pressure in the reaction vessel relative to atmospheric and proving a route for the pressurized reaction mixture to exit the reaction vessel. In one embodiment of the present invention nitrogen gas is pumped into the reaction vessel and the reaction mixture is forced from the reaction vessel through an appropriate grade of tubing. As the reaction mixture exits the reaction vessel it is passed though a filter into the mold. The filled mold is then maintained at approximately 78° C.±2° C. for 18 to 24 hours. Next the molds are transferred to a dry heat curing oven equilibrated to approximately 90° C. The molds are held at this temperature for an additional 22 to 24 hours. At this point solid, soft acrylic polymer sheets are now ready to be processed further to form AC-IOL having various diopters as known to those skilled in the art. The materials used to prepare a preferred embodiment of the present invention are summarized in the following table:

| Polymer Ingredient | Mass Percent[1] |
|---|---|
| Ethyl Acrylate (EA) | 53.57 |
| Ethyl Methacrylate (EMA) | 30.19 |
| Trifluoroethyl methacrylate (TFEMA) | 9.74 |
| Ethyleneglycol dimethacrylate (EGDMA) | 4.90 |
| Cyasorb ® UV 416 (UV Chromophore) | 1.50 |
| Trigonox ® 141 (Thermal initiator) | 0.11 |

[1]Mass percents may not total to exactly 100% due to rounding errors.

The biocompatible polymeric materials made in accordance with the teachings of the present invention suitable for use in fabricating AC-IOLs should possess the following physical characteristics:

| Glass Transition Point (Tg) ° C.[2] | Tensile Strength (PSI)[3] | Elongation at Break (%)[3] |
|---|---|---|
| 16.6–17.2 | 1680–1720 | 110–120 |

[2]Method and instrumentation for determining Tg as expressed herein include: Instrumentation: TA Instruments (New Castle, Delaware, USA) thermal analyzer Model Q1000 modulated differential scanning calorimeter (mDSC). Heating Profile: Equilibrate at - 50 C for five minutes. Modulate +/- 0.663 C/50 sec Ramp at 5 C/min to 70 C.
[3]Methods and instrumentation for mechanical properties (Tensile, % Elongation at Break) determinations as expressed herein include: Instrument = MST QTest 5 Sample Die = ASTM 0412 "C" Temperature = 20 – 25 C Pull Rate = 20 inches/minute Number of Samples Averaged = 9 per test condition In a preferred embodiment the biocompatible polymer of the present invention possesses the following physical characteristics: Tg 16.9° C.; Tensile Strength 1689 psi; Elongation at Break: 111%. Thus, disclosed herein are biocompatible polymeric compositions useful in fabricating intraocular lenses intended for implantation into the anterior chamber of both phakic and aphakic eyes. Moreover the AC-IOLs made in accordance with the teachings of the present invention have a refractive index ($n_D$) at 20° C.-25° C. of between approximately 1.40 and 1.50. In a preferred embodiment the AC-IOL has a refractive index ($n_D$) at 20° C.-25° C. of approximately 1.47.

The biocompatible polymeric compositions of the present invention provide uniquely balanced properties that make them especially useful in fabricating thin, pliable AC-IOLs that have excellent mechanical strength and durability. The AC-IOLs made having the physical characteristics disclosed above will be pliable enough to be easily folded, rolled or other wise deformed sufficiently for insertion through small incisions, have the mechanical strength necessary to absorb incidental impact after implantation and be strong enough to permit the lenses to be sufficiently thin to fit comfortably within the phakic eye's anterior chamber and while being suitable for correcting myopia, hyperopia, presbyopia and astigmatisms.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention.

All U.S. Patent Applications, Patents and references mentioned above are herein incorporated by reference in their entirety for all purposes.

What is claimed:

1. A biocompatible polymer comprising:
   50 mass percent to 55 mass percent of a first alkyl acrylate,
   29 mass percent to 32 mass percent of a second alkyl acrylate,
   9 mass percent to 11 mass percent of a fluoroacrylate,
   4 mass percent to 5 mass percent of a diacrylate ester crosslinking agent;
   wherein said biocompatible polymer is used to form an anterior chamber intraocular lens (AC-IOL).

2. The biocompatible polymer according to clam 1 wherein said first alkyl acrylate and said second alkyl acrylate are selected from the group consisting of, ethyl methacrylate, n-butyl acrylate, ethyl acrylate and 2-ethyl hexyl acrylate, providing that said first acrylate ester is different than said second acrylate ester.

3. The biocompatible polymer according to claim 1 wherein said diacrylate ester crosslinking agent is selected from the group consisting of ethylene glycol dimethacrylate, propylene glycol dimethacrylate, ethylene glycol diacrylate and combinations thereof.

4. The biocompatible polymer according to claim 1 wherein said fluoroacrylate is selected from the group consisting of periluorooctal methacrylate, trifluoroethyl methacrylate and combinations thereof.

5. The biocompatible polymer according to claim 1 further comprising at least one ultraviolet (UV) light absorbing compound.

6. The biocompatible polymer according to claim 5 further comprising a blue-violet light absorbing compound.

7. The biocompatible polymer according to claim 2 where in said first alkyl acrylate is ethyl acrylate and said second alkyl acrylate is ethyl methacrylate.

8. The biocompatible polymer according to claim 3 wherein said diacrylate ester crosslinking agent is ethylene glycol dimethacrylate.

9. The biocompatible polymer according to claim 4 wherein said fluoroacrylate is trifluoroethyl methacrylate.

10. The biocompatible polymer according to claim 1 wherein said
    first alkyl acrylate is present in a mass percent of approximately 54 mass percent,
    said second alkyl acrylate is present in a mass percent of approximately 30 mass percent,
    said fluoroacrylate is present in a mass percent of approximately 10 mass percent, and
    said diacrylate ester crosslinking agent is present in a mass percent of approximately 5 mass percent;
    wherein residual solvents and UV absorbing compounds make up the remaining mass percentage such the total mass percent is 100.

11. A biocompatible polymer comprising:
    50 mass percent to 55 mass percent of ethyl acrylate,
    29 mass percent to 32 mass percent of ethyl methacrylate,
    9 mass percent to 11 mass percent of trifluoroethyl methacrylate,
    4 mass percent to 5 mass percent of ethylene glycol dimethacrylate;
    wherein said biocompatible polymer is used to form an anterior chamber intraocular lens (AC-IOL).

12. The biocompatible polymer according to claim 11 further comprising at least one ultraviolet (UV) light absorbing compound.

13. The biocompatible polymer according to claim 12 further comprising a blue-violet light absorbing compound.

14. The biocompatible polymer according to claim 11 wherein:
said ethyl acrylate is present in a mass percent of approximately 54 mass percent,
said ethyl methacrylate is present in a mass percent of approximately 30 mass percent,
said trifluoroethyl methacrylate is present in a mass percent of approximately 10 mass percent, and
ethylene glycol dimethacrylate is present in a mass percent of approximately 5 mass percent;
wherein residual solvents and UV absorbing compounds make up the remaining mass percentage such the total mass percent is 100.

15. An AC-IOL comprising:
54 mass percent of ethyl acrylate,
30 mass percent of ethyl methacrylate,
10 mass percent of trifluoro methacrylate, and
5 mass percent of glycol dimethacrylate;
wherein residual solvents and UV absorbing compounds make up the remaining mass percentage such the total mass percent is 100.

16. An AC-IOL consisting essentially of
54 mass percent of ethyl acrylate,
30 mass percent of ethyl methacrylate,
10 mass percent of trifluoro methacrylate, and
5 mass percent of glycol dimethacrylate;
wherein residual solvents and UV absorbing compounds make up the remaining mass percentage such the total mass percent is 100.

17. A biocompatible polymer consisting essentially of
54 mass percent of ethyl acrylate,
30 mass percent of ethyl methacrylate,
10 mass percent of trifluoro methacrylate, and
5 mass percent of glycol dimethacrylate;
wherein residual solvents and UV absorbing compounds make up the remaining mass percentage such the total mass percent is 100 mass percent;
and wherein said biocompatible polymer is used to form an anterior chamber intraocular lens.

18. A biocompatible polymer comprising 50 mass percent to 55 mass percent of a first alkyl acrylate, 29 mass percent to 32 mass percent of a second alkyl acrylate, 9 mass percent to 11 mass percent of a fluoroacrylate, and 4 mass percent to 5 mass percent of a diacrylate ester crosslinking agent; wherein said biocompatible polymer has a Tg of approximately 17° C., a tensile strength of approximately 1690 psi; an elongation at break of approximately 110% and is used to form an anterior chamber intraocular lens (AC-IOL).

19. The biocompatible polymer according to claim 18 wherein said AC-IOL has a refractive index of between approximately 1.40 and 1.50.

20. The biocompatible polymer according to claim 19 wherein said AC-IOL has a refractive index of approximately 1.41.

* * * * *